| United States Patent [19] | [11] Patent Number: 5,075,361 |
|---|---|
| Derosa et al. | [45] Date of Patent: Dec. 24, 1991 |

[54] AMINOACID PHOSPHOALKYLATION OF ASPHALTENES FOR COMPATIBILIZATION IN BITUMINOUS LIQUIDS

[75] Inventors: Thomas F. Derosa, Passaic, N.J.; Rodney L. Sung, Fishkill, N.Y.; Benjamin J. Kaufman, Hopewell Junction, N.Y.; Eugene M. Jao, Fishkill, N.Y.

[73] Assignee: Texaco Inc., White Plains, N.Y.

[21] Appl. No.: 631,513

[22] Filed: Dec. 21, 1990

[51] Int. Cl.$^5$ ............................................. C08L 95/00
[52] U.S. Cl. .................................... 524/64; 106/284.1; 106/284.2; 106/284.4; 106/284.06
[58] Field of Search ............... 524/64, 415; 106/284.1, 106/284.2, 284.4, 284.06

[56] References Cited

U.S. PATENT DOCUMENTS 2,276,436  11/1940  Tucker et al. .................... 106/284.1
3,431,128   3/1969  Jones ................................ 106/284.4

Primary Examiner—Paul R. Michl
Assistant Examiner—Peter Szekely
Attorney, Agent, or Firm—Robert A. Kulason; James J. O'Loughlin; Vincent A. Mallare

[57] ABSTRACT

Asphaltenes isolated from bituminous products that have been bulk phosphochlorinated using phosphorous trichloride and amidated using aminoacids or aminoacid salts show enhanced dissolution properties when added to bituminous liquids or bituminous liquids blended with gasoline.

30 Claims, No Drawings

AMINOACID PHOSPHOALKYLATION OF ASPHALTENES FOR COMPATIBILIZATION IN BITUMINOUS LIQUIDS

BACKGROUND OF THE INVENTION

This invention relates to asphaltene compatibilization in natural and processed bituminous liquids utilizing pendant groups that behave as solubilizers and dispersants to said asphaltenes.

DISCLOSURE STATEMENT

The art contains many disclosures on asphaltene characterization and modification designed to compatibilize said material with bituminous liquids.

Article of FUEL, Volume 57, pgs. 25-28 (1978), teaches the art of asphaltenes compatibilization by the chemical incorporation of oxygen.

U.S. Pat. No. 4,182,613 discloses a method of compatibilizing asphaltic constituents in fuels by the addition of sediment-stabilizing alkylaryl sulfonic acids containing 10 to 70 carbon side chains.

Article of Journal of the American Oil Chemists Society, Volume 60, No 7, pgs 1349-1359 (1983), teaches the art of coal dispersion in water through the use of polyamine surfacts.

U.S. Pat. No. 4,378,230 discloses a method compatibilizing Bunker "C" oil and water emulsions using dextrins.

U.S. Pat. No. 648,328 discloses a method of generating organo-phosphorous compounds using trichlorophosphorous as the essential precursor.

British Patent 707,961 discloses methods designed to improve yields and to extend the range of applicability of producing organophosphorus compounds.

U S. patent application No. 838,745 discloses functionalizing polyethylene using trichlorophosphorous and hydrolysis of the same using water-acetone mixtures.

Japanese Patent 5 9004-690-A discloses a method of stabilizing coal slurries by the modification of coal using polyether phosphoric ester salts.

The disclosures in the forgoing patents and research articles which relate to asphaltene compatibilization, namely U.S. Pat. Nos. 4,182,613 and 4,378,230; U.S. patent applications, Ser. Nos. 648,328 and 838,745; British Patent 707,961; Japanese Patent 5 9004-690-A; Article of FUEL, Volume 57, pgs 25-28 (1978); and Article of Journal of the American Oil Chemists Society, Volume 60, No. 7, pgs 1349-1349 (1983) are incorporated herein by reference.

An object of this invention is to provide a method of stabilizing asphaltenes in Bunker "C" oil.

A further object of this invention is to provide a method of stabilizing asphaltenes in Bunker "C" oil containing Light Recycle Ga Oil.

SUMMARY OF THE INVENTION

This invention provides a method of compatibilizing asphaltenes containing bituminous liquids. The method comprises:

(a) reacting an asphaltene with phosphorous trichloride to produce a phosphorchlorinated-asphaltene containing from about 0.01% wt. % to about 20 wt. % phosphorous;

(b) reacting said phosphorchlorinated-asphaltene with equimolar amounts of aliphatic or aromatic amino acids selected from the group consisting of:

(i) an amino-thiazoleacetic acid represented by the formula:

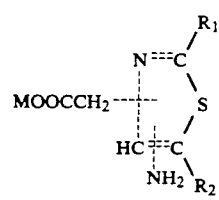

where $R_1$ and $R_2$ each are hydrogen or ($C_1$–$C_{10}$) branched or linear hydrocarbon selected from the group consisting alkyl, alkenyl, alkoxyl, alaryl, aralkyl, hydroxylalkyl, and aminoalkyl; M is hydrogen, ammonium, or a Group IA alkaline earth metal;

(ii) an aminoacid-triazoles represented by the formula:

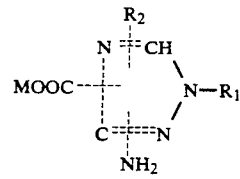

where $R_1$ and $R_2$ kare each hydrogen or ($C_1$–$C_{10}$) branched or linear hydrocarbon chains consisting of from 1 to 10 carbon atoms that may be alkyl, alkenyl, alkoxy, hydroxyalkyl, and aminoalkyl; M is hydrogen, ammonium, or a Group IA alkaline earth metal;

(iii) an alkyl benzopurpurin represented by the formula:

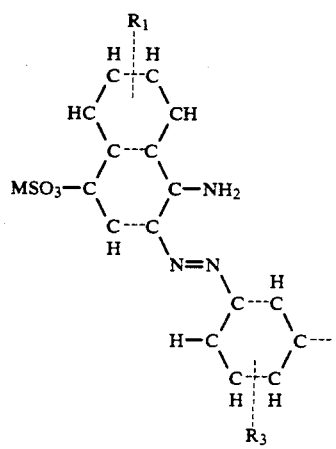

-continued

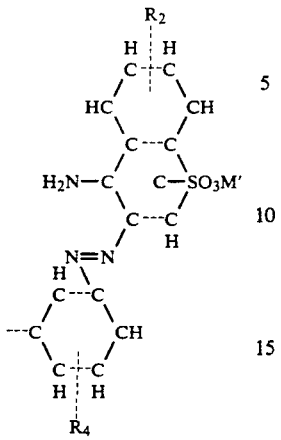

where $R_1$, $R_2$, $R_3$, and $R_4$ each are hydrogen or a branched or linear hydrocarbon selected from the group consisting of alkyl, alkenyl, alkoxyl, aralkyl, alaryl, hydroxyalkyl, and aminoalkyl; and M and M' are hydrogen, ammonium, or a Group IA alkaline earth metal;

(iv) a sulfanilic acid represented by the formula:

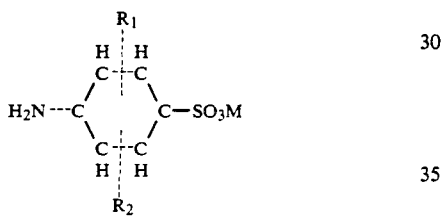

where $R_1$ and $R_2$ each are hydrogen or a ($C_1$–$C_{10}$) branched or linear hydrocarbon selected from the group containing of alkyl, alkenyl, alkoxy, aralkyl, alaryl, hydroxyalkyl, and aminoalkyl; and M represents hydrogen, ammonium, or a Group IA alkaline earth metal;

(v) a naphthylaminopolysulfonic acid represented by the formula:

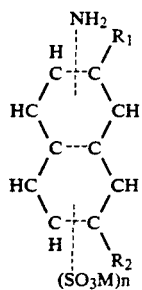

where $R_1$ and $R_2$ each are hydrogen or a ($C_1$–$C_{10}$) branched or linear hydrocarbon selected from the group consisting of alkyl, alkenyl, alkoxyl, aralkyl, alaryl, hydroxylalkyl, and aminoalkyl; n is an integer between 1 and 4; M is hydrogen, ammonium, or a Group IA metal;

(vi) an alkyl aminoacid represented by the structural formula:

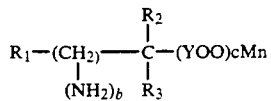

where $R_1$, $R_2$, and $R_3$ each are hydrogen or a ($C_1$–$C_{10}$) linear or branched hydrocarbon selected from the group containing of alkyl, alkenyl, alkoxyl, aralkyl, and alaryl; M is hydrogen, ammonium, or a Group IA alkaline earth metal; a, b, and c are integers ranging from 1 to 15; and n is an integer between 1 and 15;

(vii) a polyhaloaromatic aminoacid represented by the structural formula:

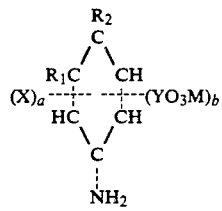

where $R_1$ and $R_2$ each are hydrogen or a ($C_1$–$C_{10}$) linear or branched hydrocarbon selected from the group consisting of alkyl, alkenyl, alkoxyl, aralkyl, alaryl, and hydroxylalkyl; X is a halide obtained from Group VIIA; Y is carbon, phosphorous, or sulfur; and a and b are integers ranging from 1 to 3; and (viii) an hydroxylated aliphatic polyacids represented by the formula:

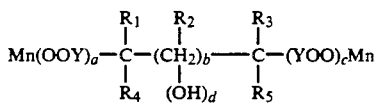

where $R_1$, $R_2$, $R_3$, $R_4$, and $R_5$ each are hydrogen or a ($C_1$–$C_{10}$) linear or branched hydrocarbon selected from the group consisting of alkyl, alkenyl, alkoxyl, aralkyl, alaryl, hydroxylalkyl, and aminoalkyl; a, b, c, and d are integers that vary from 0 to 3; Y is a Group IVA, VA, or VIA non-metal; and M is hydrogen, ammonium, or a Group IA metal to produce a compatibilized asphaltene; and (c) recovering said compatibilized asphaltene product.

Asphaltenes that have been phosphochlorinated and then post-reacted with one or more of the aforementioned amines will be characterized as being compatible with Bunker "C" oil or Bunker "C" oil blended with Light Recycle Gas Oil.

DETAILED DESCRIPTION OF THE INVENTION

Asphaltenes are components of the bitumen in petroleum, petroleum products, and other bituminous materials which are soluble in carbon disulfide but insoluble in paraffin naphtha. The physical and chemical characteristics of asphaltenes have been the subject of considerable investigation for at least a century. The asphaltene molecule appears to carry a core of approximately five stacked flat sheets of condensed aromatic rings, one above the other giving an overall height of 16–20 angstroms. The average sheet diameter appears to be about 8.5 to 15 angstroms. The molecular weight of petroleum asphaltenes ranges from about 1,000 to 10,000.

Shale oil asphaltenes appear to have a lower molecular weight.

Qualitative and semiquantitative detection of asphaltenes and bituminous liquids, e.g. petroleum and petroleum derived liquids, is conventionally carried out by observing the precipitation of asphaltenes by naphtha addition.

The presence of asphaltenes in bituminous liquid, e.g. petroleum crude, refinery streams, and other natural and processed bituminous liquids, is well known as are the problems resolving from the presence and precipitation of the asphaltenes. In petroleum production, for example, it has long been known that asphaltenes may, under some circumstances, precipitate to form a sludge which plugs up the oil bearing formation and prevents the recovery of additional petroleum. Sludge in such compositions is known to form in petroleum bearing formations, on valves, pump impellers, in conduits, and in other bituminous liquid handling equipment.

Generally, it is regarded as an advantage to keep the asphaltenes in a stable suspension in the bituminous liquid until well into the refining process. This not only increases the ultimate yield but prevents or reduces maintenance problems and also improves productivity from bituminous liquid bearing formations.

Our method for improving the compatibility of asphaltenes in Bunker "C" oil and Bunker "C" oil blends entails bulk phosphochlorination of the asphaltene followed by bulk amination of the phosphochlorinated-asphaltene intermediate. This invention constitutes a method for stabilizing asphaltenes in petroleum, shale oil, refinery streams, and other bituminous liquids. This two step process is outlined below:

Step 1. Phosphochlorination of Asphaltene

Asphaltene is initially dissolved in tetrahydrofuran (THF) and phosphochlorinated using phosphorous trichloride. Asphaltene dissolution in THF permits extensive and homogeneous asphaltene phosphochlorination.

Phosphochlorination using PCl$_3$ is shown below in Equation 1. (Eq. 1):

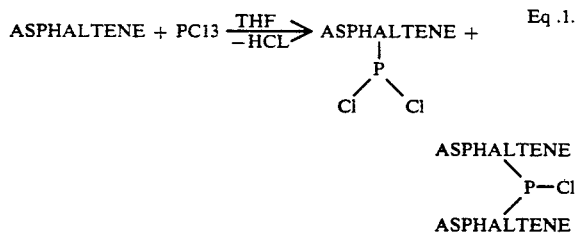

Step 2. Alkoxylation of Phosphochlorinated Asphaltene

Phosphochlorinated asphaltenes react readily with oligomeric polyethers and alcohols generating phosphoalkoxylated asphaltenes. Post-reaction of phosphochlorinated asphaltene with an oligomeric polyether diol is shown below in Equation 2 (Eq. 2):

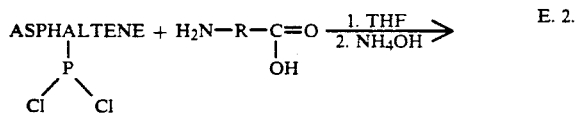

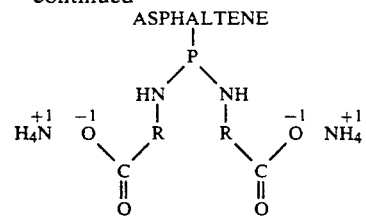

The present compatibilization procedure differs from other methods since the phosphochlorination and amination are homogeneously distributed throughout the asphaltene. Other methods are more aptly characterized as non-homogeneous surface modifications containing surface active agents.

The following examples will clarify and point out the advantages of the present invention. In the examples, experiments were performed in order to both underscore the need to chemically modify the asphaltene in order to improve compatibility in bituminous liquids. The procedures for the experiments is outlined below:

(a) Blends of 1 wt. % and 2 wt. % unmodified asphaltenes in Bunker "C" oil and Bunker "C" oil containing Light Recycle gas oil were assayed as baseline data. These test results appeal in Table 1.

(b) Blends of 1 wt. % to 2 wt. % phospho-alkoxylated asphaltenes and Bunker "C" oil and Bunker "C" oil containing Light Recycle Gas Oil were prepared and evaluated for enhanced compatibility. These tests reflect the effect of the bulk chemical modification of the asphaltene. These test results appear in Tables II, III, IV and V.

(c) Blends of physical mixtures of unmodified asphaltenes and alkyl or aromatic phosphites in bituminous liquids were evaluated for compatibility. These tests are designed to measure the effect on compatibilization alkyl or aromatic phosphite mixtures have on unmodified asphaltenes. These test results appear in Table VI.

(d) Bituminous liquids were phospho-alkoxylated and then blended with unmodified asphaltenes. These tests were designed to measure the effect on compatibilization of unmodified asphaltenes with phospho-alkoxylated bituminous liquids. These test results appear in Table VII.

(e) Alkyl- and aromatic phosphite surface active agents were incorporated onto the asphaltene surface and compatibility assayed for enhanced asphaltene compatibilization. These tests were designed to measure the effect surface active agents have upon asphaltene compatibilization in bituminous liquids. These test results appear below in Table VIII.

EXAMPLE I

Asphaltenes were obtained from Bunker "C" oil by extraction using n-heptane which were thoroughly dried and ground to a 40 mesh powder.

Phosphochlorinations were performed by adding 3 wt. % neat Pcl$_3$ to stirred solutions of 5 wt. % asphaltenes dissolved in THF at reflux temperature under anhydrous conditions. The mixture was permitted to react under these conditions from 1 to 75 hours.

Phosphochlorinated asphaltenes are isolated by removing unreacted PCl$_3$ and THF through atmospheric or vacuum distillation. This intermediate was stored under anhydrous conditions pending subsequent reaction.

EXAMPLE II

Sufficient amino-thiazoleacetic acid was dissolved in 50 to 500 mls anhydrous THF and added to phosphochlorinated asphaltenes derived from the aforementioned example to cause complete amidation to occur. The phosphoalkoxylated asphaltene was isolated through atmospheric or vacuum distillation.

Asphaltene-phosphoaminoacid salts were prepared by addition of stoichometric quantities of the corresponding base dissolved in 5:1 v/v THF and water mixture, respectively.

EXAMPLE III

In this example, amino-1,2,4-triazole-carboxylic acid was substituted for the amino-thiazole acetic acid in Example II, to produce phospho-amidated thiazole acetic acid asphaltene.

EXAMPLE IV

In this example benzopurpurin was substituted for the amino-thiazole acetic acid in Example II, to produce phosphoamidated benzopurpurin asphaltene.

EXAMPLE V

In this example sulfanic acid was substituted for the amino-thiazole acetic acid in Example II, to produce a phosphoamidated sulfanic acid asphaltene.

EXAMPLE VI

In this example, amino-naphthyldisulfonic acid was substituted in Example II, to produce a phospho-amidated naphthyldisulfonic acid asphaltene.

EXAMPLE VII

In this example, amino-azobenzene-disulfonic acid was substituted for the amino-thiazole acetic acid in Example II, to produce a phospho-amidated azolenzene-disulfonic asphaltene.

EXAMPLE VIII

In this example, aminobutyric acid was substituted for the amino-thiazole acetic acid in Example II, to produce a phosphoamidated butyric acid asphaltene.

EXAMPLE IX

In this example, aminocaproic acid was substituted for the amino-thiazole acetic acid in Example II, to produce a phosphoamidated caproic acid asphaltene.

EXAMPLE X

In this example, amino-chlorobenzoic acid was substituted for the amino-thiazale acetic acid in Example II, to produce a phospho-amidated chlorobenzoic acid asphaltene.

EXAMPLE XI

In this example, malic acid was substituted for the aminothiazole acetic acid in Example II, to produce a malic acid phosphite asphaltene.

EXAMPLE XII

Surface phosphochlorinations of asphaltenes were performed by the addition of neat $PCl_3$ to 1 to 10 wt. % stirred slurries of asphaltene in n-heptane at reflux temperatures under anhydrous conditions. Surface-phospho-chlorinated asphaltenes were isolated by filtration.

EXAMPLE XIII

Sufficient amino-thiazoleacetic acid was added to a vigorously stirred solution to cause complete surface phosphoamidation. The material was isolated by filtration.

Surface phosphoaminoacid asphaltene salts were obtained by addition of stoichiometric abounds of the corresponding base dissolved in a 1:10:10 mixture of water, 2-propinol, and N,N-dimethylformamide, respectively.

EXAMPLE XIV

In this example, amino-1,2,4-triazolecarboxylic acid was substituted for the amino-thiazoleacetic acid in Example XIII, to produce surface-phospho-amidated 1,2,4-triazole carboxylic acid asphaltene.

EXAMPLE XV

In this example, benzopurpurin was substituted for the amino-thiazoleacetic acid in Example XIII, to produce surface-phospho-amidated benxopurpurin asphaltene.

EXAMPLE XVI

In this example, sulfanilic acid was substituted for the amino-thiazoleacetic acid in Example XIII, to produce surface-phospho-amidated sulfanilic acid asphaltene.

EXAMPLE XVII

In this example, amino-naphthyldisulfonic acid was substituted for the amino thiazoleacetic acid in Example XIII, to produce surface-phospho-amidated naphthyl disulfonic acid asphaltene.

EXAMPLE XVIII

In this example, amino-azobenzene-disulfonic acid was substituted for the amino thiazoleacetic acid in Example XIII, to produce surface-phospho-amidated azobenzene-disulfonic acid asphaltene.

EXAMPLE XIX

In this example, aminobutyric acid was substituted for the amino thiazoleacetic acid in Example XIII, to produce surface-phospho-amidated butyric acid asphaltene.

EXAMPLE XX

In this example, aminocaproic acid was substituted for the amino thiazoleacetic acid in Example XIII, to produce surface phospho-amidated caproic acid asphaltene.

EXAMPLE XXI

In this example, amino-chlorobenzoic acid was substituted for the amino thiazoleacetic acid in Example XIII, to produce surface phospho-amidated chlorobenzoic acid asphaltene.

EXAMPLE XXII

In this example, malic acid was substituted for the aminothiazoleacetic acid in Example XIII, to produce surface malic acid phosphite asphaltene.

EXAMPLE XXIII

Phosphoamidations prepared in Bunker "C" oil adhered to the material stoichometry outlined in Examples I and II, above. Unmodified asphaltenes were dissolved in THF and added to Bunker "C" phosphoamidated salts; THF was removed by gently heating this mixture under atmospheric pressure.

The novel reaction products of this invention were evaluated according to the Spot Test as outlined in the ASTM D 2781 test method. In the spot test, Bunker "C" oil or Bunker "C" blend containing Light Recycle Gas Oil and the modified or unmodified asphaltene are heated to 150 "C" for a specified time and the sample removed and agitated for a specified duration. One drop of the mixture is placed onto a sheet of filter paper using a glass rod. The filter paper is baked in the oven and oil diffuses radically from the point of addition to give a uniform brown circle. Any asphaltenes which have precipitated during this process appear as a ring of darker material. The sample is rated using integers on a scale of one though five, the higher numbers indicating that precipitation has occurred.

Tables I through VIII provide a summary below of these spot test results.

TABLE I

Spot Testing Results Using ASTM Test Method D 2781 For Unmodified Asphaltene Samples Used As References.

| Sample | Spot Test Rating |
|---|---|
| 1 wt % Asphaltene + 99 wt % Bunker "C" oil | 3 |
| 2 wt % Asphaltene + 98 wt % Bunker "C" oil | 3 |
| 1 wt % Asphaltene + 99 wt % 4:1 wt/wt Light Recycle Gas Oil and Bunker "C" oil | 3 |
| 2 wt % Asphaltene + 98 wt % 4:1 wt/wt Light Recycle Gas Oil and Bunker "C" oil | 3 |

TABLE II

Spot Test Results Using ASTM Test Method D 2781 And A 1 Wt % sample In Bunker "C" Oil

| Sample | | Spot Test Rating |
|---|---|---|
| Phosphochlorinated Asphaltene + | Ammonium hydroxide | 4 |
| Phosphochlorinated Asphaltene | 2-Amino-4-thiazoleacetic acid i-Sodium Salt | 2 |
| | ii-Ammonium Salt | 2 |
| Phosphochlorinated Asphaltene | 2-Amino-1,2,4-triazole-5-carboxylic acid | 2 |
| | i-Sodium Salt | 3 |
| | ii-Ammonium Salt | 3 |
| Phosphochlorinated Asphaltene + | Benzopurpurin 4B | 1 |
| Phosphochlorinated Asphaltene + | Sulfanilic Acid | |
| | i-Sodium Salt | 1 |
| | ii-Ammonium Salt | 1 |
| Phosphochlorinated Asphaltene + | 7-Amino-1,3-naphthalenedisulfonic acid, monopotassium salt | 1 |

TABLE III

Spot Test Results Using ASTM Test Method D 2781 And A 2 Wt % Sample In Bunker "C" Oil.

| Sample | | Spot Test Rating |
|---|---|---|
| Phosphochlorinated Asphaltene + | Ammonium hydroxide | 4 |
| Phosphochlorinated Asphaltene + | 2-Amino-4-thiazoleacetic acid | |
| | i-Sodium Salt | 3 |
| | ii-Ammonium Salt | 2 |
| Phosphochlorinated Asphaltene + | 2-Amino-1,2,4-triazole-5-carboxylic acid | |
| | i-Sodium Salt | 2 |
| | ii-Ammonium Salt | 1 |
| Phosphochlorinated Asphaltene + | Benzopurpurin 4B | 1 |
| Phosphochlorinated Asphaltene + | Sulfanilic Acid | |
| | i-Sodium Salt | 1 |
| | ii-Ammonium Salt | 1 |
| Phosphochlorinated Asphaltene + | 7-Amino-1,3-naphthalenedisulfonic acid, monopotassium salt | |
| Phosphochlorinated Asphaltene + | 4-Amino-1,1'-azobenzene-3,4-disulfonic acid, sodium salt | 1 |
| Phosphochlorinated Asphaltene + | 4-Aminobutyric acid | |
| | i-Sodium Salt | 3 |
| | ii-Ammonium Salt | 2 |
| Phosphochlorinated Asphaltene + | 6-Aminocaproic acid | |
| | i-Sodium Salt | 1 |
| | ii-Ammonium Salt | 1 |
| Phosphochlorinated Asphaltene + | 5-Amino-2-chlorobenzoic acid | |
| | i-Sodium Salt | 2 |
| | ii-Ammonium Salt | 2 |
| Phosphochlorinated Asphaltene + | Malic Acid | |
| | i-Disodium Salt | 4 |
| | ii-Diammonium Salt | 3 |

TABLE IV

Spot test results using ASTM D 2781 and a 1 wt % sample in a 4:1 wt/wt blend of Light Recycle Gas Oil and Bunker "C" oil, respectively.

| Sample | | Spot Test Rating |
|---|---|---|
| Phosphochlorinated Asphaltene + | Ammonium Hydroxide | 4 |
| Phosphochlorinated Asphaltene + | 2-Amino-4-thiazoleacetic acid | |
| | i-Sodium Salt | 2 |
| | ii-Ammonium Salt | 2 |
| Phosphochlorinated Asphaltene + | 2-Amino-1,2,4-triazole-5-carboxylic Acid | |
| | i-Sodium Salt, | 2 |
| | ii-Ammonium Salt | 2 |
| Phosphochlorinated Asphaltene + | Benzopurpurin 4B | 1 |
| Phosphochlorinated Asphaltene + | Sulfanilic Acid | |
| | i-Sodium Salt | 1 |
| | ii-Ammonium Salt | 1 |
| Phosphochlorinated Asphaltene + | 7-Amino-1,3 naphthalene disulfonic acid, monopotassium salt | 1 |
| Phosphochlorinated Asphaltene + | 4-Amino-1,1'-azobenzene-3,4-disulfonic acid, sodium salt | 1 |
| Phosphochlorinated Asphaltene + | 4-Aminobutyric acid | |
| | i-Sodium Salt | 2 |
| | ii-Ammonium Salt | 1 |
| Phosphochlorinated Asphaltene + | 6-Aminocaproic acid | 1 |
| | i-Sodium Salt | 1 |
| | ii-Ammonium Salt | |
| Phosphochlorinated Asphaltene + | 5-Amino-2-chlorobenzoic acid | |
| | i-Sodium Salt | 1 |
| | ii-Ammonium salt | 1 |
| Phosphochlorinated Asphaltene + | Malic acid | |

TABLE IV-continued

Spot test results using ASTM Test Method D 2781 and a 1 wt % sample in a 4:1 wt/wt blend of Light Recycle Gas Oil and Bunker "C" oil, respectively.

| Sample | | Spot Test Rating |
|---|---|---|
| | i-Disodium Salt | 3 |
| | ii-Diammonium Salt | 2 |

TABLE V

Spot Test Results Using ASTM Test Method D 2781 And A 2 wt % Sample In A 4:1 wt/wt Blend Of Light Recycle Gas Oil And Bunker "C" oil, respectively.

| Sample | | Spot Test Rating |
|---|---|---|
| Phosphochlorinated Asphaltene + | Ammonium Hydroxide | 3 |
| Phosphochlorinated Asphaltene + | 2-Amino-4-thiazoleacetic acid | |
| | i-Sodium Salt | 2 |
| | ii-Ammonium Salt | 3 |
| Phosphochlorinated Asphaltene + | 2-Amino-1,2,4-triazole-5-carboxylic acid | |
| | i-Sodium Salt | 2 |
| | ii-Ammonium Salt | 1 |
| Phosphochlorinated Asphaltene + | Benzopurpurin 4B | 1 |
| Phosphochlorinated Asphaltene + | Sulfanilic acid | |
| | i-Sodium Salt | 1 |
| | ii-Ammonium Salt | 1 |
| Phosphochlorinated Asphaltene + | 7-Amino-1,3-naphthalenedisulfonic acid, monopotassium salt | 1 |
| Phosphochlorinated Asphaltene + | 4-Amino-1,1'-azo-benzene-3,4-disulfonic acid, sodium salt | 2 |
| Phosphochlorinated Asphaltene + | 4-Aminobutyric acid | |
| | i-Sodium Salt | 2 |
| | ii-Ammonium Salt | 1 |
| Phosphochlorinated Asphaltene + | 6-Aminocaproic acid | |
| | i-Sodium Salt | 1 |
| | ii-Ammonium Salt | 1 |
| Phosphochlorinated Asphaltene + | 5-Amino-2-chlorobenzoic acid | |
| | i-Sodium Salt | 1 |
| | ii-Ammonium Salt | 1 |
| Phosphochlorinated Asphaltene + | Malic acid | |
| | i-Disodium Salt | 2 |
| | ii-Diammonium Salt | 3 |

TABLE VI

Spot Test Results Using ASTM Test Method D 2781 For Physical Blends Containing Unmodified Asphaltenes And 1 Or 2 wt % Phosphoamidated Acid Salts In Bunker "C" Oil.

| Sample | | Spot Test Rating |
|---|---|---|
| Asphaltene + 1 wt % phosphine blend | 4-Aminobutyric acid, ammonium Salt | |
| Asphaltene + 2 wt % phosphine blend | 4-Aminobutyric acid, ammonium Salt | 3 |
| Asphaltene + 1 wt % phosphine blend | Malic acid, diammonium salt | |
| Asphaltene + 2 wt % phosphine blend | Malic acid, diammonium salt | 3 |
| Asphaltene + 1 wt % phosphine blend | 5-Amino-2-chlorobenzoic acid, ammonium salt | |
| Asphaltene + 2 wt % phosphine blend | 5-Amino-2-chlorobenzoic acid, ammonium salt | 3 |
| Asphaltene + 1 Wt % phosphine blend | 4-Amino-1,1'1 azobenzene-3,4-disulfonic acid, sodium salt | 3 |
| Asphaltene + 2 wt % phosphine blend | 4-Amino-1,1'-azobenzene-3,4-disulfonic acid, sodium salt | 3 |

TABLE VII

Spot Test Results Using ASTM Test Method D 2781 For Physical Blends Of Unmodified Asphaltenes And Phosphoamidated Acid Salts Prepared In Bunker "C" Oil.

| Sample | Spot Test Rating |
|---|---|
| Asphaltene + Bunker "C" oil w/ 1 wt % tri(Jeffamine M-2005)phosphine | 3 |
| Asphaltene + Bunker "C" oil w/ 2 wt % tri(Jeffamine M-2005)phosphine | 3 |
| Asphaltene + Bunker "C" oil w/ 1 wt % tri(n-Dodecylamino)phosphine | 3 |
| Asphaltene + Bunker "C" oil w/ 2 wt % tri(n-Dodecylamino)phosphine | |
| Asphaltene + Bunker "C" oil w/ 1 wt % tri(amino-TEMP)phosphine | 3 |
| Asphaltene + Bunker "C" oil w/ 2 wt % tri(amino-TEMP)phosphine | 3 |

TABLE VIII

Spot Testing Results Using ASTM Test Method D 2781 For Asphaltenes Containing Surface Active Agents.

| Sample | Spot Test Rating |
|---|---|
| Phosphochlorinated Asphaltene Slurry + 4-Aminobutyric acid, ammonium salt | 3 |
| Phosphochlorinated Asphaltene Slurry + Malic acid, diammonium salt | 3 |
| Phosphochlorinated Asphaltene Slurry + 5-Amono-2-chlorobenzoic acid, ammonium salt | 3 |
| Phosphochlorinated Asphaltene Slurry + 4-Amino-1,1'-azobenzene-3,4-disulfonic acid, sodium salt | 2 |

As the forgoing data indicate, acid-amidation of bulk phospho-chlorinated asphaltenes causes dramatic compatibilization in Bunker "C" oil and Bunker "C" oil blends containing Light Recycle Gas Oil, Less dramatic results are obtained by the incorporation of surface active agents onto asphaltenes. Finally, little emulsifying effect was observed by physically blending unmodified asphaltenes with Bunker "C" oil and oil blends containing phosphoamidated acid salts.

What is claimed:

1. A method of Compatibilizing asphaltenes containing bituminous liquids, comprising:
    (a) reacting an asphaltene with phosphorous trichloride to form phosphochlorinated asphaltene, containing from 0.01 weight percent to 20 weight percent phosphorous, and
    (b) reacting said phosphorchlorinated-asphaltene with equimolar amounts of aliphatic or aromatic aminoacids selected from the group consisting of:
        (i) amino-thiazoleacetic acid represented by the formula:

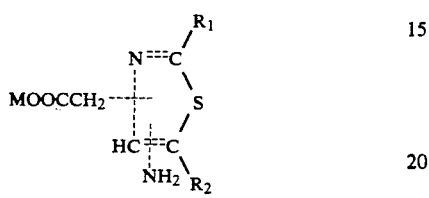

where $R^1$ and $R_2$ each are hydrogen or $(C_1-C_{10})$ branched or linear hydrocarbon groups consisting of from 1 to 10 carbon atoms that may be alkyl alkenyl, alkoxyl, alaryl, aralkyl, hydroxylalkyl, or aminoalkyl; M is hydrogen, ammonium, or a Group IA alkaline earth metal;

(ii) an aminoacid-triazole represented by the formula:

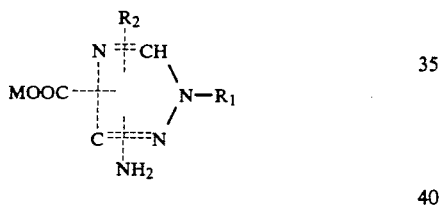

where $R_1$ and $R_2$ each are hydrogen or $(C_1-C_{10})$ branched or linear hydrocarbon of selected from the group consisting of alkyl, alkenyl, alkoxyl, hydroxyalkyl, and aminoalkyl; M is hydrogen, ammonium, or a Group IA alkaline earth metal;

(iii) an alkyl benzopurpurin represented by the formula:

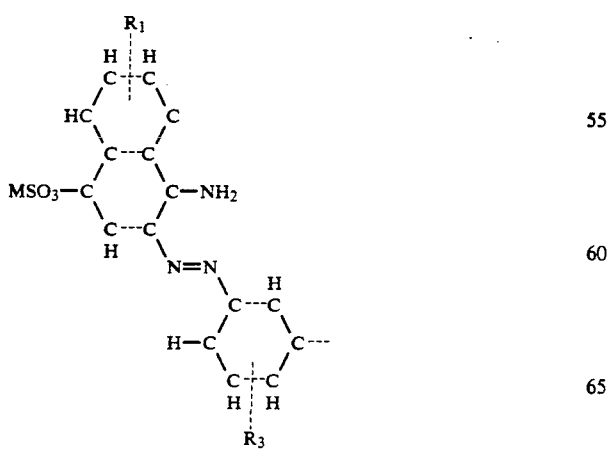

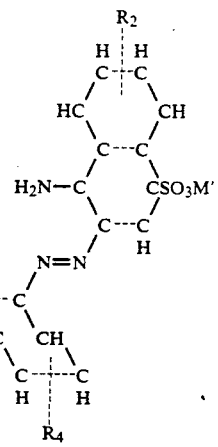

where $R_1$, $R_2$, $R_3$, and $R_4$ are hydrogen or a $(C_1-C_{10})$ branched or linear hydrocarbon selected from the group consisting of alkyl, alkenyl, alkoxy, aralkyl, alaryl, hydroxyalkyl, and aminoalkyl; and M and M' are hydrogen, ammonium, or a Group IA alkaline earth metal;

(iv) a sulfanilic acid represented by the structural formula:

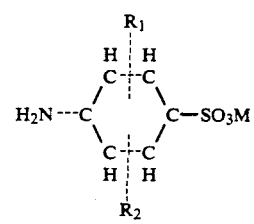

where $R_1$ and $R_2$ each are hydrogen or a $(C_1-C_{10})$ branched or linear hydrocarbon selected from the group consisting of alkyl, alkenyl, alkoxyl, aralkyl, alaryl, hydroxylalkyl, and aminoalkyl; and M is hydrogen, ammonium, or a Group IA metal;

(v) a naphthylaminopolysulfonic acid represented by the structural formula:

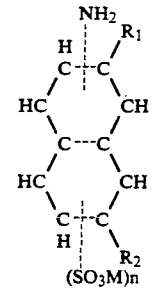

where $R_1$ and $R_2$ each are hydrogen or a $(C_1-C_{10})$ branched or linear hydrocarbon selected from the group consisting of alkyl, alkenyl, alkoxyl, aralkyl, alaryl, hydroxylalkyl, and aminoalkyl; n is an integer between 1 and 4; M is hydrogen, ammonium, or a Group IA alkaline earth metal (vi) an alkyl aminoacid represented by the formula:

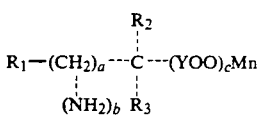

where $R_1$, $R_2$, and $R_3$ each are hydrogen or a linear or branched hydrocarbon selected from the group consisting of alkyl, alkenyl, alkoxyl, aralkyl, or alaryl; M is hydrogen, ammonium, or a Group IA alkaline earth metal; a, b, and c are integers ranging from 1 to 15; and n is an integer between 1 and 15;

(vii) a polyhaloaromatic aminoacid represented by the structural formula:

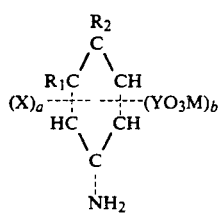

where $R_1$ and $R_2$ each are hydrogen or a ($C_1$–$C_{10}$) linear or branched hydrocarbon selected from the group consisting of alkyl, alkenyl, alkoxyl, aralkyl, alaryl, and hydroxylalkyl; X is a halide obtained from Group VIIA metal; Y is phosphorous, or sulfur; and a and b are integers that range from 1 to 3; and (viii) an hydroxylated aliphatic polyacids represented by the structural formula:

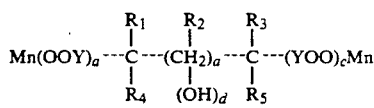

where $R_1$, $R_2$, $R_3$, $R_4$, and $R_5$ are hydrogen or a ($C_1$–$C_{10}$) linear or branched hydrocarbon selected from the groups consisting of alkyl, alkenyl, alkoxyl, aralkyl, alaryl, hydroxylalkyl, and aminohydroxyl; a, b, c, and d are integers varying from 0 to 3; Y is a Group IVA, VA, or VIA non-metal; and M is hydrogen, ammonium, or a Group IA alkalene earth metal to produce a compatibilized asphaltene; and (c) recovering said asphaltene product.

2. The method of claim 1 wherein said phosphorous content is from 0.10 weight percent to 10 weight percent.

3. The method of claim 1 wherein said phosphorous content is from 1 weight percent to 5 weight percent.

4. The method of claim 1 wherein said amino-thiazoleacetic acid is 2-amino.

5. The method according to claim 1 in which said aminoacid-triazole is 2-amino-1,2,4-triazole-5-carboxylic acid.

6. The method according to claim 1 in which said alkyl-benzopurpurin is Benzopurpurin 4B.

7. The method according to claim 1 in which said sulfanilic acid is sulfanilic acid 8. The method according to claim 1 in which said naphthyl-aminopolysulfonic acid is 7-amino-1,3-naphthalenedisulfonic acid.

9. The method according to claim 1 in which said alkyl aminoacid is 4-amino-butyric acid.

10. The method according to claim 1 in which said alkyl aminoacid is 6-amino-caproic acid.

11. The method according to claim 1 in which said polyhaloaromatic aminoacid is 5-amino-2-chlorobenzoic acid.

12. The method according to claim 1 in which said hydroxylated aliphatic polyacid is malic acid.

13. The method according to claim 1 in which said amino-thiazole-acetic acid is 2-amino-4-triazoleacetic acid.

14. The method according to claim 1 in which said aminoacid-triazole is 2-amino-1,2,4-triazole-5-carboxylic acid.

15. The method according to claim 1 in which said alkyl-benzopurpurin is Benzopurpurin 4B.

16. The method according to claim 1 in which said sulfanilic acid is sulfanilic acid.

17. The method according to claim 1 in which said naphthyl-aminopolysulfonic acid is 7-amino-1,3-naphthalenedisulfonic acid.

18. The method according to claim 1 in which said alkyl aminoacid is 4-amino-butyric acid.

19. The method according to claim 1 in which said alkyl aminoacid is 6-amino-caproic acid.

20. The method according to claim 2 in which said polyhaloaromatic aminoacid is 5-amino-2-chlorobenzoic acid.

21. The method according to claim 1 in which said hydroxylated aliphatic polyacid is malic acid.

22. The method according to claim 1 in which said amino-thiazoleacetic acid is 2-amino-4-thiazoleacetic acid.

23. The method according to claim 1 in which said aminoacid-triazole is 2-amino-1,2,4-triazole-5-carboxylic acid.

24. The method according to claim 1 in which said alkyl-benzopurpurin is Benzopurpurin 4B.

25. The method according to claim 1 in which said sulfanilic acid is sulfanilic acid.

26. The method according to claim 1 in which said naphthyl-aminopolysulfonic acid is 7-amino-1,3-naphthalenedisulfonic acid.

27. The method according to claim 1 in which said alkyl aminoacid is 4-amino-butyric acid.

28. The method according to claim 1 in which said alkyl aminoacid is 6-amino-caproic acid.

29. The method according to claim 1 in which said polyhaloaromatic aminoacid is 5-amino-2-chlorobenzoic acid.

30. The method according to claim 1 in which said hydroxylated aliphatic polyacid is malic acid.

* * * * *